United States Patent
Ackermann et al.

(10) Patent No.: US 6,977,310 B2
(45) Date of Patent: Dec. 20, 2005

(54) METHOD FOR THE CONTINUOUS PRODUCTION OF ALKYL (METH) ACRYLATES

(75) Inventors: Jochen Ackermann, Darmstadt (DE); Udo Gropp, Heppenheim (DE); Horst Hiltner, Heppenheim (DE); Hans-Rolf Rausch, Luling, LA (US); Ingrid Lunt-Rieg, Frankfurt (DE); Hermann Siegert, Seeheim-Jugenheim (DE); Ruediger Carloff, Darmstadt (DE)

(73) Assignee: Roehm GmbH & Co. KG, Darmstadt (DE)

(*) Notice: Subject to any disclaimer, the term of this patent is extended or adjusted under 35 U.S.C. 154(b) by 0 days.

(21) Appl. No.: 10/500,288

(22) PCT Filed: Dec. 6, 2002

(86) PCT No.: PCT/EP02/13828
§ 371 (c)(1),
(2), (4) Date: Jan. 12, 2005

(87) PCT Pub. No.: WO03/055837
PCT Pub. Date: Jul. 10, 2003

(65) Prior Publication Data
US 2005/0119500 A1 Jun. 2, 2005

(30) Foreign Application Priority Data
Jan. 4, 2002 (DE) .......................... 102 00 171

(51) Int. Cl.⁷ .............................................. C07C 67/02
(52) U.S. Cl. ..................................................... 560/217
(58) Field of Search ........................................ 560/217

(56) References Cited

U.S. PATENT DOCUMENTS 3,686,268 A * 8/1972 Jobert et al. ................. 558/444
5,072,027 A   12/1991 Kobayashi et al.

FOREIGN PATENT DOCUMENTS

EP    0902017    3/1999
EP    0968995    1/2000

* cited by examiner

*Primary Examiner*—Paul A. Zucker
(74) *Attorney, Agent, or Firm*—Oblon, Spivak, McClelland, Maier & Neustadt, P.C.

(57) ABSTRACT

The invention relates to a process for continuous preparation of alkyl (meth)acrylates by transesterification of methyl (meth)acrylate using alcohols which are high-boiling relative to methanol. A particular workup technique achieves product qualities which have hitherto not been attained. Very high space-time and overall yields can also be achieved.

18 Claims, 1 Drawing Sheet

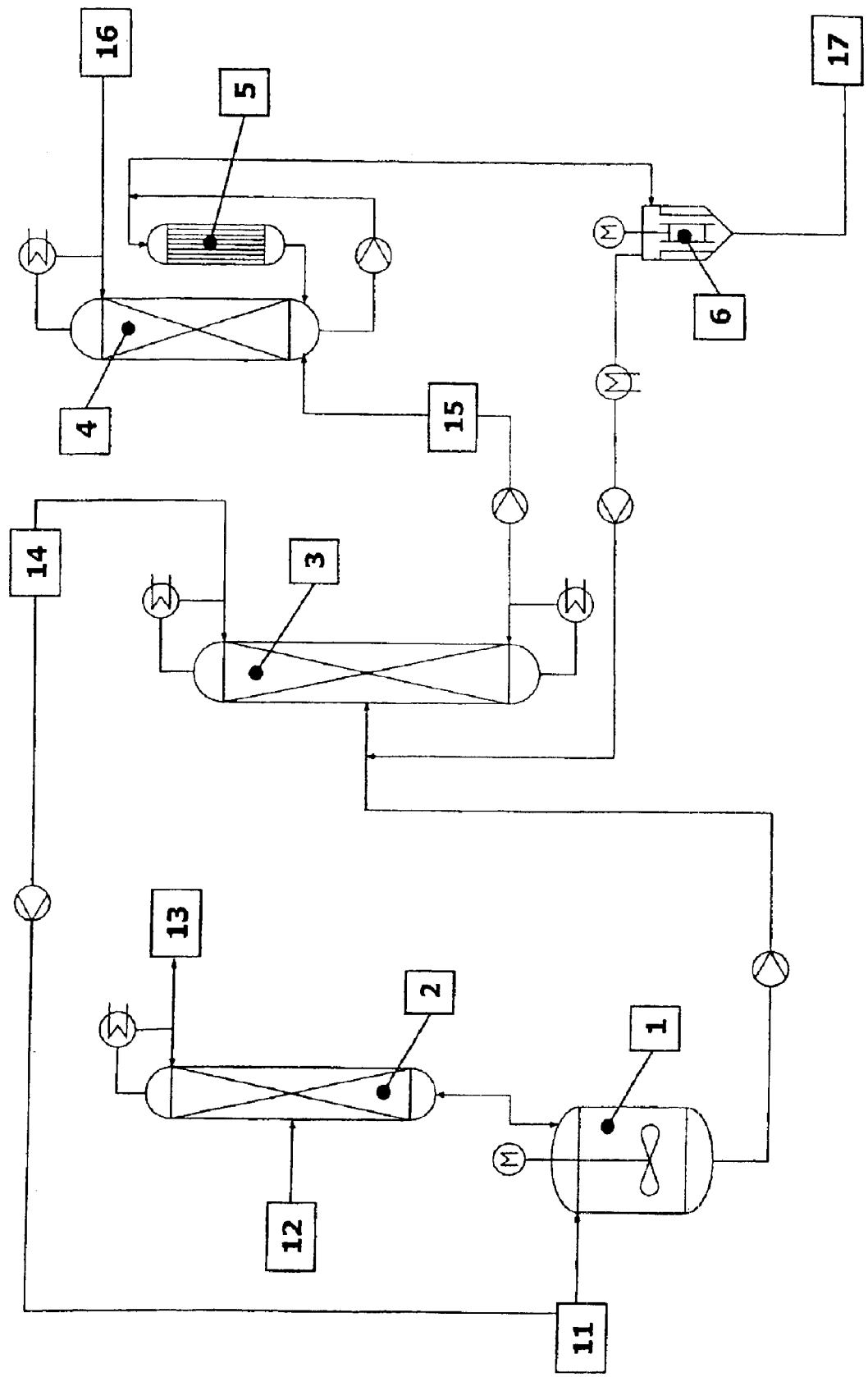

METHOD FOR THE CONTINUOUS PRODUCTION OF ALKYL (METH) ACRYLATES

FIELD OF THE INVENTION

The present invention relates to a further continuous process for preparing alkyl (meth)acrylates (C) by continuously transesterifying methyl (meth)acrylate (A) with alcohols (B) to release methanol (D) according to the following reaction equation:

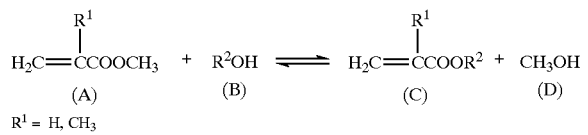

where $R_2$ is a linear, branched or cyclic alkyl radical or aryl radical having 2 to 12 carbon atoms. Examples of useful alcohols $R_2OH$ include ethanol, propanol or isopropanol, butanol or isobutanol, pentanol, cyclohexanol or hexanol, heptanol, octanol or isooctanol and 2-ethylhexanol. Other useful alcohols include isoborneol, benzyl alcohol, tetrahydrofurfural, allyl alcohol, ethylene glycol, 3,3,4-trimethylcyclohexanol, phenylethanol, butylene diglycol, tert-butylaminoethanol, diethylaminoethanol, ethylene triglycol, methylene triglycol, butyl diglycol and isopropylideneglycerol.

PRIOR ART

Alkyl (meth)acrylates may be prepared by different methods:

By reaction of acetone cyanohydrin with alcohols in the presence of sulphuric acid or by transesterification of methyl (meth)acrylate with alcohols in the presence of a catalyst. In the transesterification, both homogeneous and heterogeneous catalysts are used. Frequently, the reaction is carried out in the presence of a tetraalkyl titanate (tetraalkoxytitanium). The methanol released in the reaction is removed from the reactor with the aid of a distillation column to remove it from the reaction mixture in order to positively influence the reaction equilibrium.

The literature discloses many transesterification processes carried out batchwise (batch transesterification processes) in conjunction with different catalysts.

The search for more economic processes led to the discovery of continuous transesterification processes in which the reactants are continuously fed in and the products continuously removed. The continuous transesterification processes have the following advantages over the batchwise transesterification processes: the demands of control and regulation are lower, the personnel requirement is lower, the product quality is better and less variable, and the plant capacity increases owing to the absence of the sequential execution of the individual preparation steps (charging, reaction, low boiler removal, product removal, emptying).

Continuous transesterification processes are well known.

EP 0 960 877 (Elf Atochem S.A.) describes a continuous process for preparing methacrylate esters from dialkylaminoalcohols. Dialkylaminoalcohols are generally reacted with methyl (meth)acrylate to obtain the dialkylaminoalkyl (meth)acrylate by the following process:

The mixture of starting materials (methyl(meth)acrylate and dialkylaminoalcohol) is continuously fed to a stirred reactor together with a tetraalkyl titanate transesterification catalyst (for example tetrabutyl titanate, tetraethyl titanate or tetra(2-ethylhexyl)titanate) and at least one polymerization inhibitor (for example phenothiazine, tert-butylcatechol, hydroquinone monomethyl ether or hydroquinone), and the conversion to the dialkylamino (meth)acrylate is effected in the stirred reactor at a temperature of 90–120° C. while continuously removing the azeotropic methyl (meth) acrylate/methanol mixture. The crude reaction mixture (crude ester) is fed to a first distillation column in which, under reduced pressure, a substantially catalyst-free stream is withdrawn overhead, and the catalyst and also a little dialkylaminoalkyl (meth)acrylate are removed at the bottom of the distillation column. The top stream of the first distillation column is then fed to a second distillation column in which, under reduced pressure, a stream of low-boiling products comprising a little dialkylaminoalkyl (meth)acrylate is withdrawn overhead and a stream consisting mainly of dialkylaminoalkyl (meth)acrylate and also polymerization inhibitor(s) is removed at the bottom and is fed to a third distillation column. In the third distillation column, a rectification is carried out under reduced pressure in which the desired pure dialkylaminoalkyl (meth)acrylate ester is withdrawn overhead and essentially the polymerization inhibitor or the polymerization inhibitors are withdrawn at the bottom. After further purification with the aid of a film evaporator, the bottom stream of the first distillation column is recycled into the reactor, like the top stream from the second distillation column.

This process dispenses with dewatering of the alcohols before use which can have effects ranging from more significant deactivation of the tetraalkyl titanate used as a consequence of hydrolysis to the formation of undesired solid precipitates. The process has the further disadvantage that in the first distillation column, the catalyst is thermally stressed at relatively high temperatures in the liquid phase. This can easily lead to decomposition of the catalyst. In this process, both the unconverted reactants and the product are rectified overhead twice in total. This entails very high energy costs and a total of four rectification columns, some of which have to have very large dimensions. The process is accordingly burdened with very high capital investment and operating costs.

EP 0 968 995 (Mitsubishi Gas Chemical Comp.) describes a continuous process for preparing alkyl (meth)acrylates using a reaction column. The transesterification is effected directly within a distillation column (i.e. reactor and distillation column for removing the methyl (meth)acrylate/methanol azeotrope form one apparatus), into which the starting materials (methyl (meth)acrylate and alcohol) are fed continuously. The necessary catalyst, here likewise preferably a titanium compound, is in the distillation column. In the case of a homogeneous catalyst, the catalyst is continuously metered into the distillation column. However, owing to a flushing effect of the liquid reflux in a distillation column, the use of homogeneous catalysts in the distillation column leads to increased catalyst consumption and also, when a solid catalyst precipitate occurs, to fouling of the column internals. In the case of a heterogeneous catalyst, the catalyst is in the reaction column. However, the positioning of the catalyst in the distillation column is disadvantageous because an increased pressure drop then occurs in the distillation column and very high additional costs and inconvenience are associated with regular cleaning of the distillation column. Also, heterogeneous catalysts may deactivate, for example as a consequence of undesired polymerization.

BRIEF DESCRIPTION OF THE DRAWINGS

The process is schematically illustrated in FIG. 1.

OBJECT

It is therefore an object of the present invention to provide a continuous process for transesterifying methyl (meth) acrylate with high-boiling alcohols relative to methanol which avoids the disadvantages of the two abovementioned processes. (Meth)acrylic esters and alkyl (meth)acrylates refer hereinbelow to esters and derivatives of acrylic acid and methacrylic acid. The novel process shall also provide a product which has a better quality than those hitherto on the market. A novel process shall also provide alkyl (meth) acrylates at very low cost and inconvenience and with greater energy efficiency (i.e. more cost-effectively).

This object, and also further objects not illustrated in detail but which can be inferred or derived without further information from the introductory discussion of the prior art, are achieved by a process having the features of claim 1. Protection of advantageous derivations of the process according to the invention is claimed in the claims referring back to claim 1.

Key for FIG. 1:
1. Reaction apparatus
2. Azeotrope distillation column
3. Low boiler distillation column
4. High boiler distillation column
5. Film evaporator
6. Film evaporator
11. Methyl (meth)acrylate and catalyst feed
12. Alcohol feed
13. Methanol/methyl (meth)acrylate azeotrope
14. Low boiler cycle stream
15. Crude ester
16. Pure ester
17. High boilers and catalyst The reactants methyl (meth)acrylate (MMA, 11) and alcohol (12) are fed continuously to a suitable reaction apparatus (1) which may be either a single reaction tank or else a battery of two or more reaction tanks connected in series. It is sensible that all reaction tanks should have a vapour takeoff to the azeotrope distillation column (2) for removing the methanol released in the reaction.

The tetraalkyl titanate required as catalyst (the tetraalkoxytitanium content relative to MMA used is preferably 0.2–0.5% by weight) is preferably metered continuously into the reaction apparatus (1), as is the polymerization inhibitor(s). However, the transesterification catalysts used may also be any transesterification catalysts disclosed by the prior art. Examples of useful catalysts include zirconium acetylacetonate and further 1,3-diketonates of zirconium, and mixtures of alkali metal cyanates or alkali metal thiocyanates and alkali metal halides may also be used, and also zinc compounds, alkaline earth metal oxides or alkaline earth metal hydroxides, for example CaO, Ca(OH)$_2$, MgO, Mg(OH)$_2$ or mixtures of the abovementioned compounds, and also alkali metal hydroxides, alkali metal alkoxides and lithium chloride and lithium hydroxide, and mixtures of the abovementioned compounds with the above-mentioned alkaline earth metal compounds and the lithium salts may also be used, dialkyltin oxides, alkali metal carbonates, alkali metal carbonates together with quaternary ammonium salts, for example tetrabutylammonium hydroxide or hexa-decyltrimethylammonium bromide, and also mixed catalysts of diorganyltin oxide and organyltin halide, acidic ion exchangers, phosphorous-molybdenum heteropolyacids, titanium alkoxides, chelate compounds of the metals titanium, zirconium, iron or zinc with 1,3-dicarbonyl compounds, and lead compounds, for example lead oxides, lead hydroxides, lead alkoxides, lead carbonates or lead salts of carboxylic acids.

Examples of polymerization inhibitors include hydroquinone monomethyl ether in combination with oxygen.

The alcohol used may contain water. The amount of water in the alcohol used in the case of n-butanol is 50 to 500 ppm (0.05–0.005% by weight). Before entry into the reaction apparatus, preference is given to distillatively dewatering the alcohol using the azeotrope column (2). The water contained in the alcohol is removed overhead. To avoid contamination of the methanol/MMA azeotrope (13) with the alcohol used, the alchol is preferably added in the lower section of the distillation column (2). The alcohol used may also be dewatered in other ways:

using an upstream dewatering distillation column or
  by treating with a dewatering agent, for example a molecular sieve, or
  by a membrane separating process, for example a pervaporation.

The dewatering is significant because the water contained in the alcohol can lead to irreversible damage of the catalyst (for example tetraalkyl titanate) in the reactor. This dewatering step avoids the hydrolysis of the catalyst and the costs resulting from increased catalyst use quantities and from problems with solid precipitates. The reaction is effected in the reaction apparatus at a temperature in the range of 80 to 160° C. Preference is given to the temperature range of 110 to 135° C. To positively influence the reaction equilibrium, the methanol released in the reaction is removed from the reaction mixture as an azeotrope with MMA (13) using the distillation column (2). The reaction mixture which consists predominantly of the product alkyl (meth)acrylate, unconverted MMA and alcohol and also small amounts of methanol, the catalyst, the polymerization inhibitors and a very low proportion of by-products is fed to a continuously operated low boiler distillation column (3) after about 0.5–3 hours of reactor residence time (preference is given to a residence time of 0.75–1.5 hours). Components which are low-boiling relative to the product ester, predominantly methanol, MMA and unconverted reactant alcohol are removed there under reduced pressure, preferably in the range of 20–200 mbar. These components are removed overhead in the distillation column and recycled into the reactor region (14). This cycle stream guarantees that, based on the overall process, there is virtually complete conversion with regard to the reactants MMA and alcohol. The crude ester (15) which is obtained at the bottom of the distillation column (3) and is still contaminated with catalyst, polymerization inhibitor and high-boiling by-products preferably comprises >98% by weight of product ester and is fed continuously for workup to a further vacuum distillation stage (4, 5) which operates in the preferred pressure range of 20 to 200 mbar. The highly pure product ester is continuously distillatively removed as the top product (16).

When a conventional vacuum distillation column as described in the prior art is used for removing the catalyst and the polymerization inhibitors and also the high-boiling by-products from the crude ester (15), excessively high thermal stress in the bottom of the column results in decomposition of the catalyst and therefore release of the reactant alcohol and sometimes also the formation of ethers of the reactant alcohol. Both compounds (reactant alcohol and ether of the reactant alcohol) are low-boiling components with respect to the product ester and therefore occur as an impurity in the product ester which distinctly reduces the product quality. This problem may be solved by using an apparatus having gentle film evaporation (5) to remove the product ester from the catalyst and the polymerization inhibitors and also the high-boiling by-products. Useful apparatus for this purpose include falling-film, thin-film and short-path evaporators.

A further downstream high boiler distillation stage (4) serves to achieve the highest product ester purity (product ester >99.9% by weight, alcohol <120 ppm, MMA <10 ppm, ether <5 ppm, colour number (apha) <1). In this context, a single apparatus employing film evaporation has the disadvantage of offering insufficient purifying performance so that high-boiling by-products occur in the pure product ester (16). This problem is solved by positioning a vacuum rectification column (4) for removing the high-boiling by-products from the pure product ester above the apparatus employing film evaporation.

After removing the catalyst and the polymerization inhibitors and also the high-boiling by-products from the crude ester, a certain proportion of product ester remains in the bottom product, so that the bottom effluent is still able to flow and be conveyed efficiently. In order to minimize the loss of product ester when discharging catalyst and high-boiling by-products (17), there should be a downstream vacuum evaporation stage (6) which operates in the preferred pressure range of 20-200 mbar. Useful apparatus for this task is again an apparatus employing film evaporation. Useful apparatus for this purpose again includes falling-film, thin-film and short-path evaporators. Owing to an excessive content of high-boiling components, the product ester removed overhead in the evaporating stage does not fulfil the required specification for the pure product ester. Furthermore, owing to the thermal decomposition of the catalyst, it also contains reactant alcohol and sometimes also ethers of the reactant alcohol. For these reasons, the aim of recovering the product ester from the distillate stream cannot be achieved by recycling it directly into the high boiler distillation column, but rather by recycling to the reaction apparatus (1) or advantageously to the low boiler distillation column (3) in order to remove the low boilers before the first evaporation stage (5).

The process according to the invention is illustrated by the examples which follow without being limited to them.

The reported examples were carried out in an experimental plant on the pilot plant scale (throughput per hour: 6–8 kg of feed (MMA and alcohol) and 5–6 kg of product ester). The construction of the experimental plant was as illustrated in FIG. 1 and as described in the process description.

The reaction apparatus (1) used was a steam-heated non-mechanically stirred stainless steel reaction tank having a maximum fill volume of 15 l. The reactor was connected via a vapour line to an azeotrope distillation column (2) mounted above. The azeotrope distillation column (top pressure=1 $bar_{abs}$) was a pilot plant glass column of H=2 m and diameter of D=0.1 m packed with Sulzer CY metal fabric packings. The feed for the reactant alcohol was disposed in the middle of the column (H=1 m). The reactor effluent was fed continuously to a low boiler distillation column (3). This distillation column was a pilot plant vacuum glass column (top pressure=120 $mbar_{abs}$) of H=3.8 m and diameter D=0.1 m packed with Sulzer CY metal fabric packings. The feed was at H=2 m. The bottom was heated by means of steam. The condensed top takeoff (cycle stream) (14) was recycled continuously to the reactor. Instead of the falling-film evaporator (5) shown in FIG. 1, the continuous workup of the bottom effluent of the low boiler distillation column (15) was carried out using a thermal oil-heated glass thin-film evaporator having an evaporator surface area A=0.1 $m^2$. The vapours of this glass thin-film evaporator were passed continuously into a high boiler distillation column (4) mounted above. This was a pilot plant vacuum glass column (top pressure=120 $mbar_{abs}$) of H=0.5 m and diameter D=0.05 m packed with Sulzer CY metal fabric packings. The bottom effluent was fed continuously to a second, smaller, likewise thermal oil-heated glass thin-film evaporator (6) (top pressure=120 $mbar_{abs}$) having an evaporator surface area A=0.02 $m^2$. The vapours of this second glass thin-film evaporator were condensed out and, combined with the reactor effluent, fed continuously to the low boiler distillation column. The bottom effluent (17) was continuously discharged from the process.

The reactants (MMA and alcohol) were metered in continuously by means of piston metering pumps, and the catalyst (tetraalkyl titanate) was metered in dissolved in (water-free as per the specification) MMA feed. The MMA/catalyst feed was fed directly to the reactor, and the alcohol feed introduced preheated (to the internal column temperature) to the middle of the azeotrope distillation column.

The continuous addition of 50–100 g/h of stabilizer solution (0.2% by weight of hydroquinone monomethyl ether in MMA or product ester) into the reflux stream of the distillation columns was effected with the aid of hose pumps.

The continuous conveyance of the streams between the parts of the plant was effected either with the aid of piston metering pumps or by the sucking effect of the vacuum. Intermediate vessels (buffer volumes) were avoided as far as possible.

The composition of the streams (MMA, alcohol, MeOH and product ester contents) were determined with the aid of a gas chromatograph.

EXAMPLE 1

Continuous Preparation of n-butyl Methacrylate

To continuously prepare n-butyl methacrylate (n-BuMA), 4 kg/h of MMA/catalyst feed having a tetra-n-butyl titanate (Ti(n-OBu)$_4$) content of 0.45% by weight and 2.7 kg/h of n-BuOH feed were metered into the reaction tank. The recycle stream from the top of the low boiler distillation column also flowed continuously into the reactor (2.8 kg/h having the following composition: 1.0% by weight of n-BuMA, 38.3% by weight of n-BuOH, 57.3% by weight of MMA and 3.4% by weight of MeOH). The molar MMA:n-BuOH ratio in the reactor feed was 1.1:1. At a reactor residence time of 1 h and an MMA/MeOH azeotrope takeoff of 1.5 kg/h, a reactor temperature of 115° C. was attained. The composition of the MMA/MeOH azeotrope was 82% by weight of MeOH, 18% by weight of MMA and <5 ppm of n-BuOH. The resulting reactor effluent of 8 kg/h had the following composition: 64.6% by weight of n-BuMA, 13.5% by weight of n-BuOH, 20.3% by weight of MMA, 1.3% by weight of MeOH and 0.3% by weight of by-products. The space-time yield of the reactor based on n-BuMA was therefore 570 kg/h/$m^3$. Owing to virtually complete removal of low-boiling components relative to n-BuMA, the bottom effluent of the low boiler distillation column was a crude ester (5.8 kg/h) which already comprised >99.5% by weight of n-BuMA and also all of the catalyst and the stabilizer. The yield of n-BuOH based on the overall process was therefore virtually 100%. The yield of MMA based on the overall process minus the MMA loss via the MMA/MeOH azeotrope calculated beforehand was likewise virtually 100%. At an evaporation ratio (ratio of vapour to feedstream) in the first, larger thin-film evaporator of about 90%, 5.1 kg/h of pure n-BuMA are finally obtained at the top of the high boiler distillation column and have the following composition: >99.92% by weight of n-BuMA, <120 ppm of n-BuOH, <10 ppm of MMA, <5 ppm of di-n-butyl ether, colour number (apha) <0.2. At an evaporation ratio in the second, smaller thin-film evaporator of about 90%, the overall discharge of the process (catalyst, stabilizer, high-boiling by-products, n-BuMA) is 0.1 kg/h and the yield loss of n-BuMA based on the pure n-BuMA produced is <0.5% by weight.

EXAMPLE 2

Continuous Preparation of Isobutyl Methacrylate

To continuously prepare isobutyl methacrylate (i-BuMA), 3.4 kg/h of MMA/catalyst feed having a tetra-i-butyl titanate (Ti(i-OBu)$_4$) content of 0.56% by weight and 2.36 kg/h of i-BuOH feed were metered into the reaction tank. The recycle stream from the top of the low boiler distillation column also flowed continuously into the reactor (2.4 kg/h having the following composition: 6.2% by weight of i-BuMA, 35.3% by weight of i-BuOH, 56.3% by weight of MMA and 2.2% by weight of MeOH). The molar MMA:i-BuOH ratio in the reactor feed was 1.1:1. At a reactor residence time of 1.2 h and an MMA/MeOH azeotrope takeoff of 1.26 kg/h, a reactor temperature of 115° C. was attained. The composition of the MMA/MeOH azeotrope was 82% by weight of MeOH, 18% by weight of MMA and <5 ppm of i-BuOH. The resulting reactor effluent of 6.9 kg/h had the following composition: 67.3% by weight of i-BuMA, 12.0% by weight of i-BuOH, 19.4% by weight of MMA, 0.8% by weight of MeOH and 0.5% by weight of by-products. The space-time yield of the reactor based on i-BuMA was therefore 516 kg/h/m$^3$. Owing to virtually complete removal of low-boiling components relative to i-BuMA, the bottom effluent of the low boiler distillation column was a crude ester (5.0 kg/h) which already comprised >99.5% by weight of i-BuMA and also all of the catalyst and the stabilizer. The yield of i-BuOH based on the overall process was therefore virtually 100%. The yield of MMA based on the overall process minus the MMA loss over the MMA/MeOH azeotrope calculated beforehand was likewise virtually 100%. At an evaporation ratio (ratio of vapour to feedstream) in the first, larger thin-film evaporator of about 90%, 4.5 kg/h of pure i-BuMA are finally obtained at the top of the high boiler distillation column and have the following composition: >99.9% by weight of i-BuMA, <150 ppm of i-BuOH, <10 ppm of MMA, <0 ppm of di-i-butyl ether, colour number (apha) <0.2. At an evaporation ratio in the second, smaller thin-film evaporator of about 90%, the overall discharge of the process (catalyst, stabilizer, high-boiling by-products, i-BuMA) is 0.05 kg/h and the yield loss of i-BuMA based on the pure i-BuMA produced is <0.5% by weight.

What is claimed is:

1. Process for continuously preparing alkyl (meth)acrylates of the formula (C)

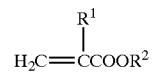

(C)

where R$_1$ is an H or CH$_3$ group and R$_2$ is a linear, branched or cyclic alkyl radical or aryl radical having from 2 to 12 carbon atoms by reacting a compound of the formula (B)

R$^2$OH                                              (B)

where R$_2$ is as defined above with methyl (meth)acrylate (A)

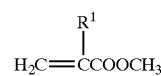

(A)

where R$_1$ is an H or CH$_3$ group in the presence of a transesterification catalyst and in the presence of at least one polymerization inhibitor in an apparatus for continuous transesterification,
characterized in that
the reactants are continuously fed to a suitable reaction apparatus (1) and that the methanol resulting from the reaction is continuously removed as an azeotropic methanol/methyl (meth)acrylate mixture (13) with the aid of a distillation column (2), and also:
the reaction mixture is continuously conducted from the reaction apparatus into a distillation column (3) in which distillation under reduced pressure is used to remove the volatile components (A, B, methanol) and a very low proportion of product ester (C) overhead which are recycled into the reaction apparatus and to remove the product ester (C) together with the catalyst and the polymerization inhibitors and also high-boiling by-products from the bottom of the column;
the bottom stream (15) from the distillation column (3) is fed continuously to an evaporator (5) in which distillation under reduced pressure is used to separate the product ester (C) from the catalyst and the polymerization inhibitors and also high-boiling by-products.

2. Process according to claim 1,
characterized in that
the vapour stream of the evaporator (5) is fed continuously to a distillation column (4) in which distillation under reduced pressure is used to remove the highly pure product ester (C) (16) overhead and to remove the catalyst and the polymerization inhibitors and also the high-boiling by-products with a small portion of product ester (C) via the bottom.

3. Process according to claim 1,
characterized in that
the bottom stream of the distillation column (4) and of the evaporator (5) is fed continuously to a further film evaporator (6) in which distillation under reduced pressure is used to remove the catalyst and the polymerization inhibitors and also the high-boiling by-products via the bottom and to remove the remaining product ester (C) overhead which is then recycled to the distillation column (3) or to the reaction apparatus (1).

4. Process according to claim 1,
characterized in that
the alcohol (B) is fed to the reaction apparatus via the distillation column (2) for dewatering.

5. Process according to claim 1, characterized in that
the molar ratio of methyl (meth)acrylate to alcohol in the feed to the reactor is from 1 to 2.

6. Process according to claim 1, characterized in that
the transesterification catalyst used is a tetraalkyl titanate.

7. Process according to claim 1, characterized in that
the catalyst is used in an amount of 0.1–2% by weight, based on MMA used.

8. Process according to claim 7, characterized in that
the catalyst is used in an amount of 0.2–1% by weight, based on MMA used.

9. Process according to claim 1, characterized in that
the polymerization inhibitor used is either phenothiazine, tert-butylcatechol, hydroquinone monomethyl ether, hydroquinone or a mixture thereof in an amount of 100 to 5000 ppm, based on the reaction mixture.

10. Process according to claim 1, characterized in that
oxygen is additionally used as a polymerization inhibitor.

11. Process according to claim 1, characterized in that
the alcohol used is n-butanol or isobutanol.

12. Process according to claim 1, characterized in that
the pressure in the first distillation column (3) is 20 to 200 mbar.

13. Process according to claim 1, characterized in that
the pressure in the second distillation column (4) and in the film evaporators (5) (6) is 20 to 200 mbar.

14. Process according to claim 1, characterized in that
the residence time in the reaction apparatus is 0.5 to 1.5 hours.

15. Process according to claim 1, characterized in that
the evaporator (5) is a film evaporator.

16. Process according to claim 3, characterized in that
the evaporator (5) and the evaporator (6) are film evaporators.

17. Process according to claim 1, characterized in that
the alcohol used is 2-ethylhexanol.

18. Process according to claim 1, characterized in that the molar ratio of methyl (meth)acrylate to alcohol in the feed to the reactor is from 1.05 to 1.15.

* * * * *

UNITED STATES PATENT AND TRADEMARK OFFICE
CERTIFICATE OF CORRECTION

PATENT NO. : 6,977,310 B2
DATED : December 20, 2005
INVENTOR(S) : Ackermann et al.

It is certified that error appears in the above-identified patent and that said Letters Patent is hereby corrected as shown below:

Title page,
Item [75], Inventors, should read:
-- Jochen Ackermann, Darmstadt (DE); Udo Gropp, Heppenheim (DE); Horst Hiltner, Heppenheim (DE); Hans-Rolf Lausch, Luling, LA (US); Ingrid Lunt-Rieg, Frankfurt (DE); Hermann Siegert, Seeheim-Jugenheim (DE); Ruediger Carloff, Darmstadt (DE) --.

Signed and Sealed this

Fourteenth Day of February, 2006

JON W. DUDAS
*Director of the United States Patent and Trademark Office*